United States Patent [19]
Parkes

[11] 4,112,940
[45] Sep. 12, 1978

[54] SCAVENGING VALVE DEVICE
[75] Inventor: Alvin E. Parkes, Lewisburg, W. Va.
[73] Assignee: The Raymond Lee Organization, Inc., New York, N.Y. ; a part interest
[21] Appl. No.: 762,462
[22] Filed: Jan. 25, 1977
[51] Int. Cl.[2] .............................................. A61M 17/00
[52] U.S. Cl. ................................... 128/188; 128/276; 137/604
[58] Field of Search .................. 128/188, 145.8, 145.7, 128/145.6, 202, 209, 210, 276, 277, 278, 274, 139, 247; 137/604, 605

[56] References Cited
U.S. PATENT DOCUMENTS

| | | | |
|---|---|---|---|
| 3,155,107 | 11/1964 | Woodford | 128/247 X |
| 3,191,600 | 6/1965 | Everett | 128/276 |
| 3,800,793 | 4/1974 | Marrese et al. | 128/188 |
| 3,998,227 | 12/1976 | Holbrook et al. | 128/276 |

Primary Examiner—Henry J. Recla
Attorney, Agent, or Firm—Daniel Jay Tick

[57] ABSTRACT

A scavenging valve for anesthesia gas release in pediatric anesthesia apparatus is of generally conical configuration and has an axial bore extending therethrough from an open base to an open apex with a plurality of longitudinally extending fins around the bore in the valve. The scavenging valve has a plurality of external fin-like projections at its base. Each of the fin-like projections has a hole formed therethrough for facilitating releasable affixing of the scavenging valve to an operating table to prevent shifting of the valve. A control valve comprises a pair of nipples each of generally conical configuration in base to base relation with an axial bore extending therethrough from one open apex end to the other. The control valve has a radially extending hole formed therethrough at the juncture of the bases of the nipples. The bore tapers down to each of the apices from the bases. The control valve couples an anesthesia bag to the scavenging valve and has a gas flow control and shutoff plate pivotally mounted in the bore thereof in the area of the bases of the control valve. A manually operable control member is provided outside the control valve. A pin extends through the hole through the control valve and couples the control member to the valve plate in a manner whereby the valve plate rotates in correspondence with rotation of the control member.

2 Claims, 4 Drawing Figures

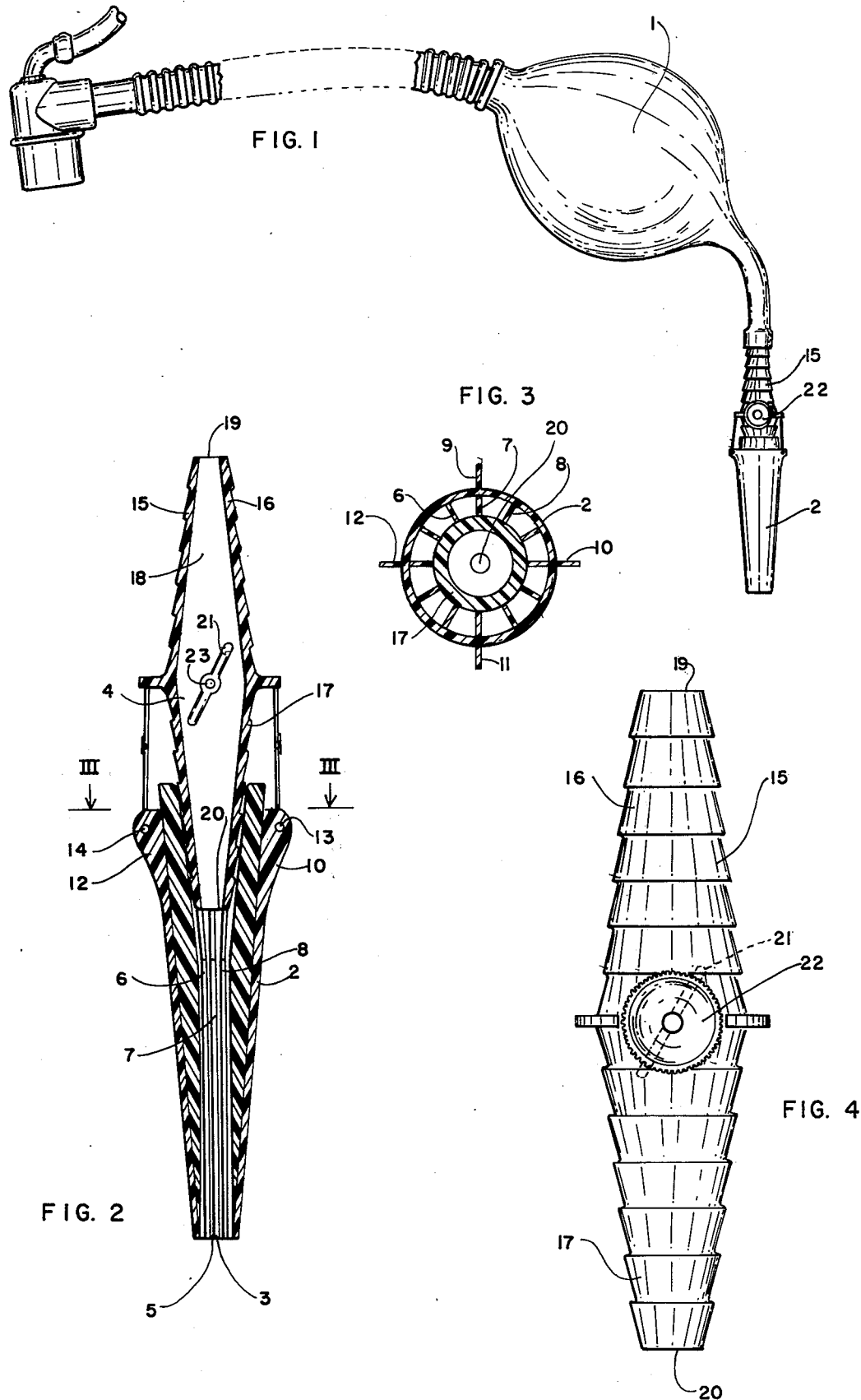

SCAVENGING VALVE DEVICE

BACKGROUND OF THE INVENTION

The present invention relates to a scavenging valve device. More particularly, the invention relates to a scavenging valve device for anesthesia gas release in pediatric anesthesia apparatus having an anesthesia bag.

Objects of the invention are to provide a scavenging valve device of simple structure, which is inexpensive in manufacture, used with facility and convenience, completely safe in operation, and functions efficiently, effectively and reliably to permit the securing of the valve to an operating table during a surgical procedure to eliminate shifting around of such valve.

BRIEF DESCRIPTION OF THE DRAWINGS

In order that the invention may be readily carried into effect, it will now be described with reference to the accompanying drawings, wherein:

FIG. 1 is a view of an embodiment of the scavenging valve device of the invention in pediatric anesthesia apparatus;

FIG. 2 is a view, on an enlarged scale, of the embodiment of the scavenging valve device of FIG. 1;

FIG. 3 is a view, on an enlarged scale, taken along the lines III—III, of FIG. 2; and FIG. 4 is a view, on an enlarged scale, of the embodiment of FIGS. 1 and 2 of the control valve.

DETAILED DESCRIPTION OF THE INVENTION

The scavenging valve device of the invention is for anesthesia gas release in pediatric anesthesia apparatus of the type shown in FIG. 1 having an anesthesia bag 1 which contains anesthesia in gas form.

The scavenging valve device of the invention comprises a scavenging valve 2 (FIGS. 1 to 3) of generally conical configuration having an axial bore 3 extending therethrough from an open base 4 to an open apex 5 with a plurality of longitudinally extending fins 6, 7, 8, and so on (FIGS. 2 and 3), around the bore in the valve.

The scavenging valve 2 has a plurality of external fin-like projections 9, 10, 11 and 12 at its base, all of which are shown in FIG. 3 and the projections 10 and 12 are shown in FIG. 2. Each of the fin-like projections 9 to 12 has a hole formed therethrough for facilitating releasable affixing of the scavenging valve 2 to an operating table to prevent shifting of said valve. The holes 13 and 14 of the fin-like projections 10 and 12 respectively, are shown in FIG. 2. This enables a chain, wire, cord, or the like, to be passed through the holes of the fin-like projections to secure the scavenging valve 2 to an operating table during a surgical procedure thereby preventing shifting of the valve and thus preventing leakage of anesthesia gas and the resultant serious consequences of its affecting of the surgeons and doctors in attendance.

The scavenging valve device of the invention further comprises a control valve 15 (FIGS. 1, 2 and 4) comprising a pair of nipples 16 and 17 (FIGS. 2 and 4). Each of the nipples 16 and 17 is of generally conical configuration in base to base relation. An axial bore 18 (FIG. 2) extends through the control valve 15 from one open apex end 19 to the other open apex end 20 (FIGS. 2 and 4).

The control valve 15 has a radially extending hole (not shown in the views of the FIGS.) formed therethrough at the juncture of the bases of the nipples 16 and 17. The bore 18 tapers down to each of the apices 19 and 20 from the bases, as shown in FIG. 2.

The control valve 15 couples the anesthesia bag 1 to the scavenging valve 2, as shown in FIG. 1, and has a gas flow control and shutoff valve plate 21 (FIGS. 2 and 4) pivotally mounted in the bore 18 thereof in the area of the bases of the control valve. A manually operable control member 22 (FIGS. 1 and 4) is provided outside the control valve 15. A pin 23 (FIG. 2) extends through the hole through the control valve 15 and couples the control member 22 to the valve plate 21 in a manner whereby the valve plate rotates in correspondence with rotation of the control member.

The control member 22 preferably comprises a knurled wheel.

While the invention has been described by means of a specific example and in a specific embodiment, I do not wish to be limited thereto, for obvious modifications will occur to those skilled in the art without departing from the spirit and scope of the invention.

I claim:

1. A scavenging valve device for anesthesia gas release in pediatric anesthesia apparatus, said scavenging valve device comprising an anesthesia bag;

a scavenging valve of generally conical configuration having an axial bore extending therethrough from an open base to an open apex with a plurality of longitudinally extending fins around the bore in the valve, said scavenging valve having a plurality of external fin-like projections at its base, each of the fin-like projections having a hole formed therethrough for facilitating releasable affixing of the scavenging valve to an operating table to prevent shifting of said valve; and a control valve comprising a pair of nipples each of generally conical configuration in base to base relation with an axial bore extending therethrough from one open apex end to the other, the control valve having a radially extending hole formed therethrough at the juncture of the bases of the nipples, said bore tapering down to each of the apices from the bases, means for coupling one of said nipples at said control valve to said anesthesia bag and the other of said nipples within the scavenging valve, said control valve having a gas flow control and shutoff valve plate pivotally mounted in the bore thereof in the area of the bases of the control valve, a manually operable control member outside the control valve, and a pin extending through the hole through the control valve and coupling the control member to the valve plate in a manner whereby the valve plate rotates in correspondence with rotation of the control member.

2. A scavenging valve device as claimed in claim 1, wherein the control member of the control valve comprises a knurled wheel.